United States Patent
Raines

(10) Patent No.: US 11,969,602 B2
(45) Date of Patent: Apr. 30, 2024

(54) MEDICAL DEVICE LEAD CONDUCTOR TO TERMINAL INTERFACE

(71) Applicant: Advanced Neuromodulation Systems, Inc., Plano, TX (US)

(72) Inventor: Aaron Raines, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 147 days.

(21) Appl. No.: 17/460,023

(22) Filed: Aug. 27, 2021

(65) Prior Publication Data
US 2023/0064802 A1 Mar. 2, 2023

(51) Int. Cl.
*A61N 1/375* (2006.01)
*A61N 1/05* (2006.01)

(52) U.S. Cl.
CPC .......... *A61N 1/375* (2013.01); *A61N 1/0551* (2013.01)

(58) Field of Classification Search
CPC ........ A61N 1/375; A61N 1/0551; A61N 1/05; A61N 1/36125
See application file for complete search history.

(56) References Cited

U.S. PATENT DOCUMENTS

| | | | |
|---|---|---|---|
| 2012/0232623 A1* | 9/2012 | Barker | A61N 1/0551 29/825 |
| 2014/0277322 A1* | 9/2014 | Victorine | A61N 1/05 607/116 |
| 2015/0080995 A1* | 3/2015 | Seeley | A61N 1/05 607/116 |
| 2016/0243352 A1 | 8/2016 | Raines et al. | |

* cited by examiner

*Primary Examiner* — Mark W. Bockelman
(74) *Attorney, Agent, or Firm* — Norton Rose Fulbright US LLP

(57) ABSTRACT

Systems and methods which provide radial exterior weld terminal configurations for medical device leads are described. A radial exterior weld terminal may comprise an annular conductive structure having a radial exterior weld interface feature, wherein a medical device lead may comprise one or more radial exterior weld terminals. A radial exterior weld interface feature may be disposed at an end of the annular conductive structure and may configure the annular conductive structure to accept a non-axially directed portion of a conductive wire for interfacing a conductor with a weld location on an outer surface of the radial exterior weld terminal. The radial exterior weld interface feature may comprise a truncated aperture configured for the non-axially directed portion of conductive wire to traverse from the inner space to the outer surface. The truncated aperture may comprise a dimple member depressed into the interior space of the annular conductive structure.

19 Claims, 5 Drawing Sheets

MEDICAL DEVICE LEAD CONDUCTOR TO TERMINAL INTERFACE

TECHNICAL FIELD

The present invention relates to medical device leads and, more particularly, to terminal configurations of implantable electrical stimulation leads facilitating small diameter lead implementations.

BACKGROUND OF THE INVENTION

Implantable medical devices (IMDs) providing functions such as stimulation of muscle or neurological tissue and/or sensing of physiological occurrences within a human body are used for a wide variety of medical conditions. For example, IMDs in the form of implantable electrical stimulation devices have been commercially distributed that allow electrical pulses or signals to be controllably delivered to targeted tissue or nerves after implantation of the respective device within a patient. Such implantable electrical stimulation devices may be used for cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression. Various neurostimulation techniques have, for example, been shown to be helpful in treating patients with chronic intractable pain.

IMDs in the form of implantable electrical stimulation devices generally include an implanted pulse generator that generates electrical pulses or signals that are transmitted to targeted tissue or nerves through a medical device lead comprising an implantable electrical stimulation lead having electrodes. Medical device leads configured for use with IMDs, such as implantable electrical stimulation devices, typically include connector apparatus (e.g., one or more electrical contacts) disposed on a proximal end and the aforementioned electrodes (e.g., one or more electrically conductive surfaces) disposed on a distal end. Conductive wires (e.g., filars formed from stranded or solid core insulated conductors) interconnect the electrodes at the distal end to corresponding electrical contacts of the connector apparatus at a proximal end. A jacket (e.g., a flexible, resilient member formed biocompatible polymer) is typically included in the body of leads, wherein the conductive wires may be disposed within the jacket and protected from body tissue and other external agents by the jacket. An axial lumen is generally formed within the body of medical device leads (e.g., in the center of a lead body formed from the jacket and extending axially from the proximal end to a point very near a lead tip at the distal end), such as to facilitate manufacture of the lead and/or to accommodate a stylet or similar tool used in implanting the lead.

In use, the medical device lead electrodes are placed within specific areas of the patient's body to provide therapeutic treatment and/or sensing with respect to particular tissue, organs, etc. For example, whether used in a stimulation and/or sensing capacity, electrodes of medical device leads are commonly implanted within, near, adjacent, or along various tissue for providing neurostimulation therapy and/or sensing one or more aspects of the surrounding environment. Peripheral nerve stimulation (PNS) techniques, for example, dispose electrodes along peripheral nerves. As another particular example, spinal cord stimulation (SCS) techniques dispose electrodes within the epidural or intrathecal space of the spinal column. In a further example, deep brain stimulation (DBS) disposes electrodes within a specific area of the brain. Other techniques dispose electrodes of a medical device lead in and around other organs or tissue of a patient, such as around the heart.

For those patients who prove unresponsive to conservative pain management techniques, for example, PNS may be a successful therapy for pain management when the pain is known to result from a specific nerve. PNS is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. PNS typically involves a procedure in which one or more electrodes of a medical device lead are placed adjacent to a select one of the peripheral nerves. Peripheral nerves are the nerves that are located beyond the brain or spinal cord. Once implanted, the lead may be disposed to extend from the stimulation/sensing site to the location of an associated IMD (e.g., a stimulation generator or a pulse generator). The distance from the stimulation/sensing site to the IMD may, for example, be on the order of 20-100 cm. In some situations, a lead extension may be utilized between a lead and IMD in order to span relatively long distances. In operation, the one or more electrodes deliver electrical pulses as may be generated and provided by the IMD.

It should be appreciated from the foregoing that the electrodes of a medical device lead (e.g., implantable electrical stimulation leads utilized with respect to PNS, SCS, DBS, and/or other stimulation techniques) are generally precisely placed within the patient's body to achieve therapeutic efficacy and/or reduced side effects. Implantation of a medical device lead may, for example, include making an incision near a target area (e.g., stimulation/sensing site), inserting a needle (e.g., 14 gauge to 16 gauge needle) into the target area, and inserting the lead down the needle to the precise site that is to be stimulated. A stylet may be used within an axial lumen of the lead to aid in guiding the insertion of the distal end of the lead into the tissue of the target area and to precisely place the electrodes.

The size of current implantable stimulation leads can be problematic with respect various implantable solutions. For example, implantation techniques such as PNS, and even SCS, using needles to insert the lead to the precise site that is to be stimulated can demand very small diameter (e.g., 1 mm to 1.4 mm outer diameter) lead bodies and electrodes.

Medical device leads often include a plurality of electrodes (e.g., 2-16 electrodes) on the distal end and a corresponding number of conductive wires for providing connectivity between the electrodes and the same number of electrical contacts on the proximal end. In some examples, a medical device lead may include a single electrode and corresponding electrical contact. Each electrode and/or electrical contact (electrodes and electrical contacts are collectively referred to herein as terminals) may comprise an annular conductive surface (e.g., electrically conductive continuous ring, split or non-continuous ring, etc.), wherein a corresponding conductive wire is electro-conductively affixed to an interior surface thereof. Blind welding techniques (e.g., blind resistance welding or blind laser welding) are typically used to affix a conductive wire to an inner surface of a terminal of a medical device lead for electric communication.

It can be difficult to consistently and reliably blind weld conductors onto the interior surface of medical device lead terminals. The inability to sufficiently view the portion of a conductor being welded to the inner surface of a terminal has presented challenges with respect to connection of conductive wires to terminals using blind welding techniques. Moreover, the inner diameters of the terminals are small (e.g., electrode ID<1 mm to 1.4 mm in above PNS example), rendering it difficult to develop fixturing capable of consistently and reliably welding conductors to the terminals of a medical device lead. Due to the small inner diameter of the electrode and the very small wire gauge of the conductive wires (e.g., 36 AWG to 48 AWG), it can be challenging to effectively and accurately engage a conductive wire with a resistance welding apparatus to accomplish a reliable weld. Implementing laser welding can, in addition to necessitating added steps for removing insulation from a portion of the conductive wire in preparation for welding, present challenges with respect to consistently disposing the bared conductor against the inner surface of the electrode for application of laser energy to accomplish a weld.

In addition to the conductive wire that has its conductor affixed to the interior surface of a terminal, the conductive wires of other terminals are often also present within the interior space of a terminal. For example, an electrode disposed more near the proximal end of a medical device lead may not only have the conductive wire that has its conductor affixed thereto within its interior space, but may also have the conductive wires for one or more electrodes disposed more towards the distal end of the lead passing through its interior space. As a specific example, in a lead configuration having 8 electrodes, the electrode disposed most towards the proximal end of the lead may not only have its corresponding conductive wire within its interior space, but may also have the conductive wires corresponding to each of the 7 other electrodes of the medical device lead within its interior. Additionally, an appreciable portion of the interior space of an annular terminal configuration is typically consumed by the aforementioned axial lumen. Accordingly, the conductive wires of a medical device lead may be confined to a very small space in which portions of some of all of the conductive wires may be in very close proximity.

The above described welding techniques (e.g., resistance welding and laser welding) typically produces a weld spot or bead a distance from the end of the conductive wire, wherein a portion of the conductor may present a protuberance extending somewhat into the interior space of a terminal. For example, the filament conductor of a solid core conductive wire or the multiple filament strands of a stranded core conductive wire may present somewhat sharp barbs protruding into the terminal interior space from a weld point. Such barbed protrusions into the inner area of a terminal can pierce the insulation of another conductive wire, whether during manufacture or use, leading to an undesired interaction between the electrode channels.

BRIEF SUMMARY OF THE INVENTION

The present invention is directed to systems and methods which provide radial exterior weld terminal configurations for implantable electrical stimulation leads facilitating small diameter lead implementations and/or which enable consistent and reliable welding of conductors to the terminals. Radial exterior weld terminals of embodiments of the invention may, for example, be utilized as electrodes (e.g., neurostimulation and/or sensing electrodes to provide therapeutic treatment and/or sensing with respect to particular tissue) of various configurations of implantable electrical stimulation leads. Additionally or alternatively, radial exterior weld terminals of embodiments of the invention may, for example, be utilized as connectors (e.g., one or more electrical contacts to provide connectivity to an implantable electrical stimulation device) of various configurations of implantable electrical stimulation leads. Embodiments of radial exterior weld terminals implemented according to concepts herein may provide a small diameter (e.g., 1 mm to 1.4 mm outer diameter) enabling and providing medical device leads well suited for insertion into a target area via needle (e.g., 14 gauge to 16 gauge needle). Medical device leads comprising one or more radial exterior weld terminals of some embodiments of the present invention may thus be well suited for use in peripheral nerve stimulation (PNS) techniques and/or spinal cord stimulation (SCS) techniques.

Radial exterior weld terminals of embodiments of the invention may, for example, comprise an annular conductive structure having a radial exterior weld interface feature disposed thereon. A medical device lead may, for example, comprise one or more such radial exterior weld terminals along a polymeric body of the medical device lead. For example, a plurality of radial exterior weld terminals may provide an array of electrodes disposed along a distal end of the medical device lead. Additionally or alternatively, a plurality of radial exterior weld terminals may provide an array of electrical contacts disposed along a proximal end of the medical device lead. Each such electrode and/or electrical contact may comprise the aforementioned annular conductive structure having a radial exterior weld interface feature disposed thereon.

An annular conductive structure of embodiments of a radial exterior weld terminal may have an outer surface and an inner surface radially disposed with respect to an axis of the annular conductive structure. One or more conductive wires of a medical device lead, including a conductive wire used for placing the radial exterior weld terminal in communication another element of the medical device lead, may be accommodated within an inner space defined by the inner surface of the annular conductive structure.

A radial exterior weld interface feature of embodiments of a radial exterior weld terminal may be disposed at a first end of the annular conductive structure of the radial exterior weld terminal. In accordance with some examples, the radial exterior weld interface feature configures the annular conductive structure to accept a non-axially directed portion of a conductive wire disposed within an interior space of the radial exterior weld terminal for interfacing a conductor of the non-axially directed portion of the conductive wire with a weld location on an outer surface of the radial exterior weld terminal. The radial exterior weld interface feature may, for example, comprise a truncated aperture disposed with a truncation side at the first end of the annular conductive structure. The truncated aperture of embodiments may be configured for the non-axially directed portion of the respective conductive wire to traverse from the inner space to the outer surface. In accordance with some examples, the truncated aperture may comprise a dimple member depressed into the interior space of the annular conductive structure and have the weld location thereon. An edge of the dimple member may be disposed on an edge of the truncated aperture to facilitate the non-axially directed portion of the respective conductive wire traversing from the inner space to the outer surface.

A radial exterior weld terminal of embodiments of the invention is configured to allow the conductor of a conductive wire to be welded to the terminal with a non-blind weld. In particular, blind welding of the conductor within the small inner diameter of the terminal is avoided through use of configurations of a radial exterior weld terminal. A laser welding process or a resistance welding process may be used according to some examples to weld the conductor at a weld location on an outer surface of the radial exterior weld terminal. Disposing the welding location on an outer surface of the radial exterior weld terminal of embodiments allows for the weld to be inspected for a good weld to where a blind weld cannot. After welding and inspection, the weld area may be covered with polymer (e.g., a polymer forming a polymeric body of a medical device lead including the radial exterior weld terminal) during downstream processes.

In accordance with some examples herein, a radial exterior weld terminal may accommodate fixturing enabling resistance welding apparatus to effectively and accurately engage the conductive wire to consistently and reliably weld the conductor to an outer surface of the terminal. The need to strip the insulation from a conductive wire to expose the conductor for welding may be avoided using resistance welding techniques according to embodiments, thus facilitating appreciable cost savings in production time and/or yields.

Embodiments of a radial exterior weld terminal are configured to minimize the space needed within an interior space of the terminal for facilitating welding of the conductor to the terminal. Accordingly, a radial exterior weld terminal of embodiments herein may provide suitable space for readily accommodating a plurality of conductive wires (e.g., the respective conductive wires for one or more additional terminals) passing through the interior space of the terminal. Such configurations may, for example, enable and/or facilitate minimizing the diameter of the terminal (e.g., facilitating terminal diameters on the order of 1 mm outer diameter in a multiple electrode medical device lead).

A radial exterior weld terminal of embodiments of the invention is configured to position the weld location for connection of a conductive wire to the terminal toward an edge of the terminal. Accordingly, a relatively large outer surface area may be provided by radial exterior weld terminal configurations of some examples.

An embodiment of a radial exterior weld terminal of the present invention accommodates interfacing a non-axially directed portion of a conductive wire with a weld location on an outer surface of the terminal. The non-axially directed portion of the conductive wire may, for example, be directed off-axis with respect to the axis of the annular conductive structure, such as may comprise a portion of a coiled wire. In accordance with some examples, the conductive wire may comprise helically wound wire having its helix axis along the same direction as an axis of the exterior weld terminal.

A radial exterior weld terminal configuration of embodiments provides not only for a conductor being welded on an outer surface of the terminal, but also provides for the full extent of a tail portion of the conductor that extends radially beyond the weld to also being outside of the inner area of the terminal. For example, the entire tail portion of the conductor of the non-axially directed portion of the conductive wire welded to the outer surface of the terminal at the weld location may extend radially beyond the weld location outside of the interior space of the terminal. Such a configuration reduces the chance of the wire strand(s) of the conductor puncturing the insulation of other conducive wires, as may result in undesired interaction (e.g., electrical short circuits) between the electrode channels.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

DETAILED DESCRIPTION OF THE INVENTION

Figure 1A:
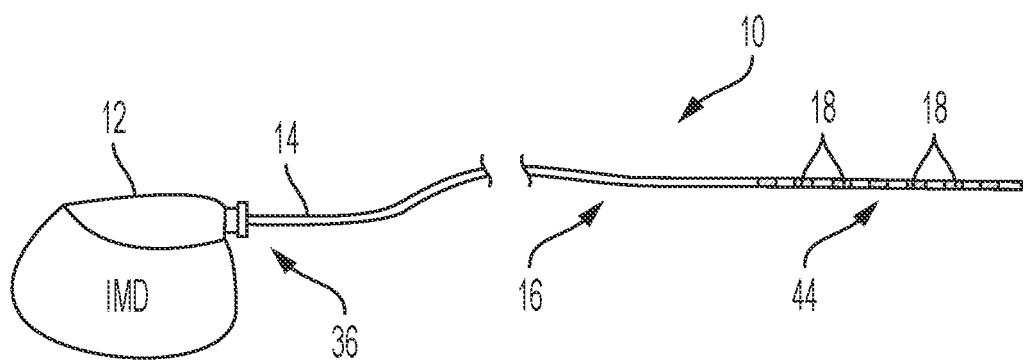
FIGS. 1A and 1B illustrate example stimulation systems as may utilize embodiments of radial exterior weld terminal configurations of embodiments of the present invention.

Radial exterior weld terminal configurations are provided according to embodiments of the invention facilitating small diameter medical device lead implementations and/or enabling consistent and reliable welding of conductors to the terminals. For example, electrodes (e.g., neurostimulation and/or sensing electrodes) of an implantable medical electrical stimulation lead may comprise radial exterior weld terminals of embodiments of the invention. As another example, connectors (e.g., one or more electrical contacts to provide connectivity to an implantable electrical stimulation device) of an implantable medical electrical stimulation lead may comprise radial exterior weld terminals of embodiments of the invention. Medical device leads comprising one or more radial exterior weld terminals of some embodiments of the present invention may, for example, be configured for use in peripheral nerve stimulation (PNS) techniques, spinal cord stimulation (SCS) techniques, deep brain stimulation (DBS) techniques, and/or other stimulation therapy, sensing, and/or monitoring techniques.

To aid in understanding concepts herein, the description that follows describes examples relating to implantable medical devices of a PNS system. However, it is to be understood that, while embodiments of a radial exterior weld terminal are well suited for applications in PNS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, spinal column stimulator, microstimulator, or in any other neural stimulator configured to treat various indications.

A radial exterior weld terminal according to concepts herein may be utilized with one or more therapy delivery elements comprising an electrical lead including one or more electrodes to deliver pulses or signals to a respective target tissue site in a patient. Additionally or alternatively, a radial exterior weld terminal may be utilized with one or more therapy delivery elements comprising an electrical lead including sensing electrodes to sense physiological parameters (e.g., blood pressure, temperature, cardiac activity, etc.) at a target tissue site within a patient.

In the various embodiments contemplated by this disclosure, therapy may include stimulation therapy, sensing, or monitoring of one or more physiological parameters, fluid delivery, and the like. A therapy delivery element (also referred to as a medical device lead or simply a lead) may include pacing or defibrillation leads, stimulation leads, sensing leads, extensions for any of the above, or combinations thereof. A target tissue site may refer generally to the target site for implantation of a therapy delivery element, regardless of the type of therapy.

Figure 1B:
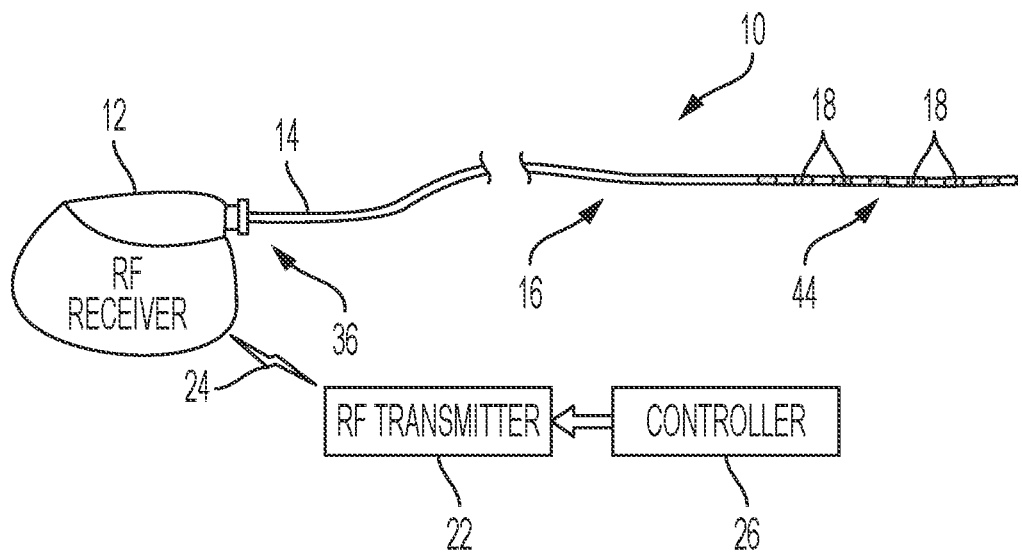

FIGS. 1A and 1B illustrate example neurological stimulation systems 10 for electrically stimulating a predetermined site, for example, a peripheral nerve, to provide therapeutic treatment and/or sensing (e.g., to treat one or more indications). In general terms, stimulation system 10 includes implantable medical device (IMD) 12 (e.g., an IMD in the form of an implantable electrical stimulation device) and one or more implantable medical device leads comprising implantable electrical stimulation leads having electrodes. IMD 12 provides a stimulation source (e.g., a pulse generator that generates electrical pulses or signals for transmission to targeted tissue or nerves). Accordingly, the illustrated example of stimulation system 10 includes electrical stimulation lead 14 for applying electrical stimulation pulses to a predetermined site. Although only one electrical stimulation lead 14 is shown, often two or more leads are used with the therapy delivery system 10.

Electrical stimulation lead 14 includes elongated body 16, such as may be composed of a suitable electrically insulative material (e.g., a polymer, such as polyurethane or silicone), having proximal end 36 and distal end 44. Elongated body 16 of electrical stimulation lead 14 of some embodiments may, for example, have a diameter of between about 1 mm to 1.8 mm and a length within the range of 30 cm to 90 cm. In the illustrated embodiment, proximal end 36 of electrical stimulation lead 14 is electrically coupled to IMD 12, such as via a connector assembly (not visible in the figures). As shown in the illustrated example, electrical stimulation lead 14 may include one or more neurostimulation electrodes 18 located on distal end 44 of elongated body 16 of the lead.

IMD 12 of embodiments may include an electronic subassembly having control and pulse generation circuitry (e.g., implantable pulse generator, not shown) for delivering electrical stimulation energy to neurostimulation electrodes 18 of electrical stimulation lead 14 in a controlled manner. IMD 12 of some examples may thus include a power supply, such as a battery. The housing of IMD 12 may be composed of a biocompatible material, such as for example titanium, forming a hermetically sealed compartment containing the electronic subassembly and power supply and providing protection from the body tissue and fluids. A connector assembly may be disposed in a portion of the housing that is, at least initially, not sealed and is configured to receive proximal end 36 of electrical stimulation lead 14 having electrical contacts configured to electrically couple the lead to an implantable pulse generator of IMD 12. The connector assembly may, for example, comprise a plurality of contacts that electrically couple with respective terminals at proximal end 36 of electrical stimulation lead 14 (or an optional extension lead, if present). Electrical conductors extend from the connector assembly and connect to the electronic subassembly of IMD 12 of examples.

In operation of stimulation system 10, IMD 12 provides a programmable stimulation signal (e.g., in the form of electrical pulses or substantially continuous-time signals) that is delivered to target stimulation sites by neurostimulation electrodes 18. Accordingly, one or both of IMD 12 and electrical stimulation lead 14 are implanted in or on a subject's body. In certain embodiments, IMD 12 is coupled to electrical stimulation lead 14, such as through one or more electrical contacts of a connector apparatus disposed on proximal end 36 of the lead. IMD 12 of some examples may be coupled to electrical stimulation lead 14 via an optional implantable extension lead (not shown). In certain other embodiments, IMD 12 is incorporated into electrical stimulation lead 14 (e.g., IMD 12 may be integrated with or embedded within electrical stimulation lead 14).

Whether IMD 12 is coupled to or incorporated into electrical stimulation lead 14, IMD 12 controls the stimulation pulses transmitted to one or more neurostimulation electrodes 18 located on distal end 44 of the lead, positioned in communication with a predetermined target area (e.g., stimulation/sensing site), according to suitable stimulation parameters (e.g., duration, amplitude or intensity, frequency, pulse width, etc.). In applications with more than one electrical stimulation lead 14, implantable pulse generator 12 may provide the same or a different signal to neurostimulation electrodes 18 for providing stimulation signals delivered to the predetermined target area.

The predetermined target area in communication with electrical stimulation lead 14 is a peripheral nerve according to some examples. Peripheral nerves can include cranial nerves for example, olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, and the hypoglossal nerve. In addition to cranial nerves, the predetermined target area can be a dermatome area, for example, C2, C3, C4, C5, C6, C7, C8, as well as any thoracic, lumbar or sacral dermatome. Other dermatomes that can be included as target areas according to embodiments of the present invention include dermatomes associated with cranial nerves having somatosensory function, for example, but not limited to dermatomes associated with the trigeminal nerve, intermediate part of the facial nerve, glossopharyngeal nerve, or vagal nerve. Peripheral nerves also include spinal nerves, which in general, are named after the vertebral segment of the spinal column above their origin. For example, the spinal nerve originating under the third thoracic vertebra may be termed the third thoracic nerve. Thus, spinal nerves can include, but are limited to cervical nerve roots (e.g., C1, C2, C3, C4, C5, C6, C7 and C8), thoracic nerve roots (e.g., T1, T2, T3, T4, T5, T6, T7, T8, T9, T10, T11, T12), lumbar nerve roots (L1, L2, L3, L4, L5) sacral nerve roots (e.g., S1, S2, S3, S4, S5) and the coccygeal nerve. Other peripheral nerves are spinal nerves such as the suboccipital nerve, the greater occipital nerve, the lesser occipital nerve, the greater auricular nerve, the lesser auricular nerve, the phrenic nerve, and the brachial plexus, which branches to form the dorsal scapular nerve, the thoracic nerve, the suprascapular nerve, the lateral pectoral, the musculocutaneous nerve, the axillary nerve, the radial nerve, the median nerve, the ulnar nerve, the intercostal nerves, and other minor peripheral nerves, as well as parasympathetic and/or sympathetic nerves. In certain embodiments, the peripheral nerve stimulated is the trigeminal nerve or the trigeminal dermatome or any peripheral nerve associated with the C2 dermatome area, C3 dermatome area, cranial nerves, the median nerve or any combination thereof. Peripheral nerve ganglia, which are collections of peripheral nerve cell bodies, may be predetermined target areas in communication with electrical stimulation lead 14 in certain embodiments.

In certain embodiments, transcutaneous implantation of electrical stimulation lead 14 is used either permanently or temporarily. Neurostimulation electrodes 18 of electrical stimulation lead 14 may, for example, be precisely placed in communication with a target area within the patient's body through a implantation technique in which an incision is made near the target area, a needle (e.g., 14 gauge to 16 gauge needle) is inserted into the target area, and distal end 44 of electrical stimulation lead 14 comprising neurostimulation electrodes 18 is inserted down the needle to the precise site that is to be stimulated. A stylet may be used within an axial lumen of electrical stimulation lead 14 to aid in guiding the insertion of the distal end of the lead into the tissue of the target area and to precisely place the electrodes.

IMD 12 may, for example, be implanted in a surgically-made pocket, such as in the abdomen or above the buttocks. IMD 12 may, of course, also be implanted in other locations of the patient's body. Use of an extension lead facilitates locating IMD 12 away from an exit point of electrical stimulation lead 14. Additionally or alternatively, and extension lead may serve as a lead adapter if proximal end 36 of electrical stimulation lead 14 is not compatible with the connector assembly of IMD 12, since different manufacturers use different connectors at the ends of their stimulation leads and are not always compatible with a connector assembly of a particular IMD.

Since IMD 12 of embodiments is located remotely from the target area for therapy, electrical stimulation lead 14 (and one or more extension leads, when present) may be routed through subcutaneously formed pathways (e.g., along the torso of the patient) to a subcutaneous pocket where IMD 12 is located.

Electrical stimulation lead 14 of embodiments may be fixed in place near the target area selected by the clinician using one or more anchors. For example, an anchor may be positioned on electrical stimulation lead 14 in a wide variety of locations and orientations along elongated body 16 to accommodate individual anatomical differences and the preferences of the clinician. In a typical implementation, an anchor may be disposed on distal end 44 of elongated body 16 on the side of neurostimulation electrodes 18 towards proximal end 36 (e.g., disposed on the distal end more near to the IMD than are the electrodes). Such an anchor may then be affixed to tissue using fasteners, such as for example, one or more sutures, staples, screws, or other fixation devices. The tissue to which an anchor is affixed may include subcutaneous fascia layer, bone, or some other type of tissue. Securing anchor 47 to tissue in this manner reduces the chance that electrical stimulation lead 14 will become dislodged or will migrate in an undesired manner.

A doctor, the patient, or another user of IMD 12 may directly or indirectly input stimulation parameters to specify or modify the nature of the stimulation provided. Some embodiments may, for example, employ a burst stimulus. In an example, burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, about 10 milliseconds to about 300 milliseconds, or any range therebetween. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

In accordance with some embodiments, IMD 12 can take the form of an implantable receiver-stimulator in which the power source for powering the implanted receiver and/or control circuitry to command the receiver-stimulator are provided externally. Control circuitry and a power source of some examples may be contained in an external controller which is inductively coupled to a receiver-stimulator configuration of IMD 12 via an electromagnetic link. IMD 12 in the embodiment shown in FIG. 1B, for example, includes an implantable wireless receiver. The wireless receiver of this example is capable of receiving wireless signals from wireless transmitter 22 operable under control of controller 26, both of which are located external to the person's body. In some embodiments, the wireless transmitter may be stand-alone and no external controller 26 is required. The wireless signals are represented in FIG. 1B by wireless link symbol 24. A doctor, the patient, or another user of IMD 12 may use controller 26 to provide control signals for operation of IMD 12. Controller 26 may, for example, provide the control signals to wireless transmitter 22, wireless transmitter 22 transmits the control signals and power to wireless receiver of IMD 12, and IMD 12 uses the control signals to vary the stimulation parameters of stimulation pulses transmitted through electrical stimulation lead 14 to the target area (e.g., predetermined peripheral nerve). Thus, external controller 26 can be for example, a handheld programmer, to provide a means for programming the IMD.

In still other embodiments, IMD 12 can take the form of an external trial stimulator (ETS), which has similar pulse generation circuitry as an implantable pulse generator (IPG), but differs in that it is a non-implantable device that is used on a trial basis after electrical stimulation lead 14 has been implanted and prior to implantation of an IPG, to test the responsiveness of the stimulation that is to be provided.

Irrespective of the particular configuration of IMD 12, electrical stimulation lead 14 of embodiments may utilize a radial exterior weld terminal configuration of the present invention with respect to one or more of electrical contacts and/or electrodes thereof. For example, neurostimulation electrodes 18 of electrical stimulation lead 14 shown in FIGS. 1A and 1B may comprises embodiments of radial exterior weld terminals implemented according to concepts herein.

Figure 2A:
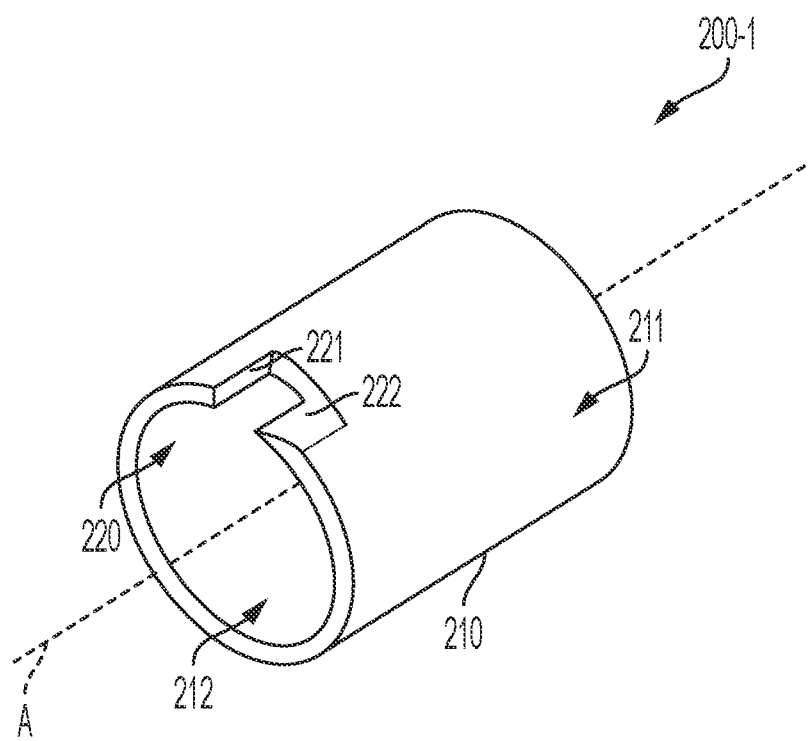
FIGS. 2A and 2B show a first example of a radial exterior weld terminal configuration of embodiments of the present invention.
Figure 2B:
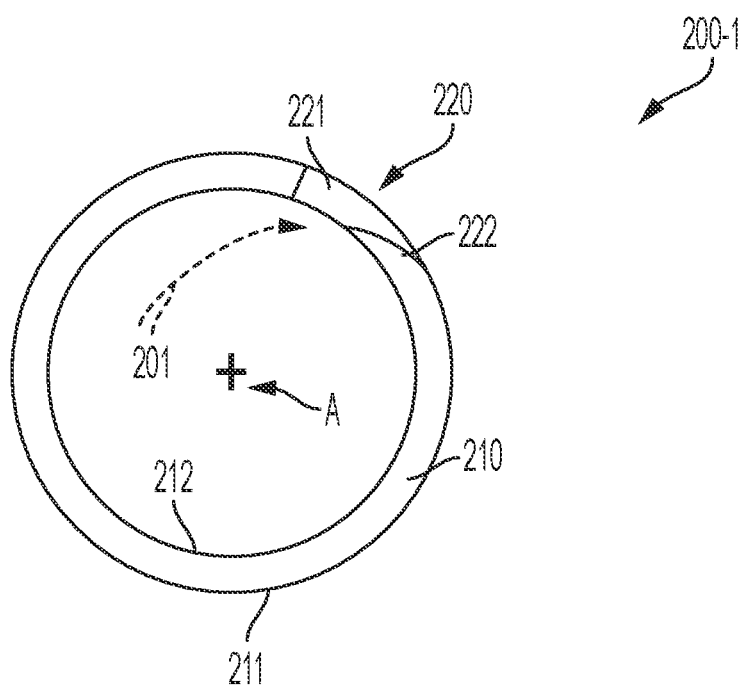
Figure 2C:
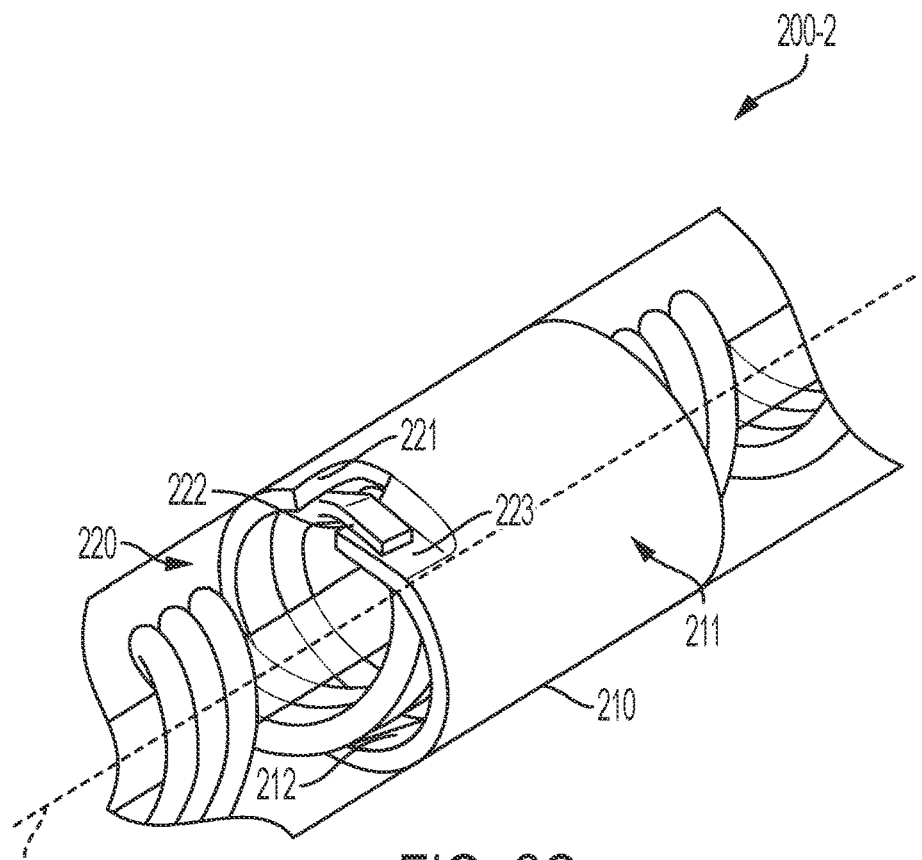
FIGS. 2C and 2D show a second example of a radial exterior weld terminal configuration of embodiments of the present invention.
Figure 2D:
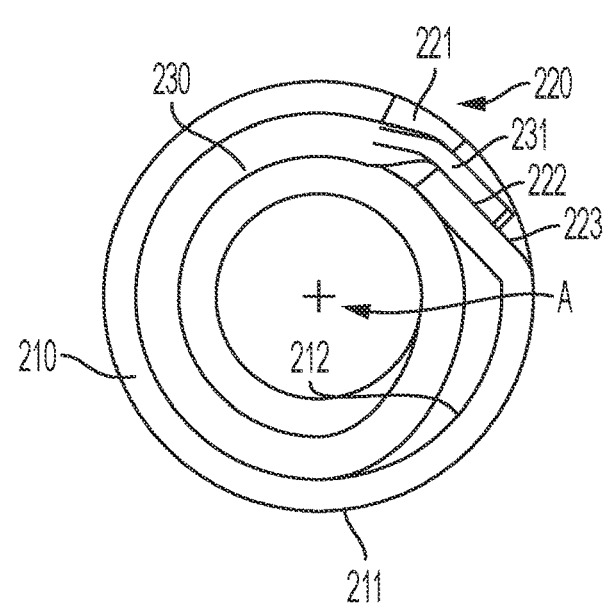

FIGS. 2A-2D show example embodiments of terminals 200 comprising radial exterior weld terminals according to concepts of the present invention. In particular, FIG. 2A shows a perspective view of terminal 200-1 of the example radial exterior weld terminal configuration of a first embodiment, while FIG. 2B shows an end view of terminal 200-1 of the example radial exterior weld terminal configuration of FIG. 2A. Similarly, FIG. 2C shows a perspective view of terminal 200-2 of the example radial exterior weld terminal configuration of a second embodiment, while FIG. 2D shows an end view of terminal 200-2 of the example radial exterior weld terminal configuration of FIG. 2C. Terminals 200 may, according to some examples, be utilized in providing various electrodes and/or electrical contacts of a medical device lead (e.g., neurostimulation electrodes 18 of electrical stimulation lead 14).

Terminals 200 (i.e., terminal 200-1 of FIGS. 2A and 2B and terminal 200-2 of FIGS. 2C and 2D) of the example radial exterior weld terminal configurations of FIGS. 2A-2D comprise annular conductive structure 210, such as may be composed of an electrically conductive biocompatible material (e.g., platinum, platinum-iridium alloy, 316 stainless steel, 35N alloy, etc.) Annular conductive structure 210 of the illustrated examples provides a generally cylindrical body in which outer surface 211 and inner surface 212 are radially disposed with respect to axis A. It should be appreciated, however, that other shapes and forms of the conductive structure (e.g., oblate, frustum, etc.) may be used to implement radial exterior weld terminal configurations of embodiments of the present invention.

Radial exterior weld interface feature 220 is provided according to the example radial exterior weld terminal configurations to facilitate electrically coupling a conductor of conductive wires to terminals 200. For example, radial exterior weld interface feature 220 of the examples is configured for interfacing a conductor of a conductive wire passing within an interior area of annular conductive structure 210 with outer surface 211. Accordingly, radial exterior weld interface feature 220 of example terminals 200 shown in FIGS. 2A-2D includes truncated aperture 221 and weld location 222 configured according to concepts herein.

Radial exterior weld interface feature 220 of embodiments is configured to minimize or mitigate reduction of an area of outer surface 211. For example, radial exterior weld interface feature 220 of the illustrated embodiments of terminals 200 is positioned at an edge of annular conductive structure 210 to provide a small aperture configured to accommodate a portion of a conductive wire passing from the interior area of annular conductive structure 210 to interface with weld location 222 on outer surface 211. According to the illustrated examples, truncated aperture 221 is disposed with a truncation side at the end of annular conductive structure 210. Correspondingly, weld location 222 is positioned toward the edge of annular conductive structure 210 for connection of a conductive wire to the terminal. Accordingly, a relatively large area of outer surface 211 may be maintained by the radial exterior weld terminal configurations of terminals 200 having radial exterior weld interface feature 220.

Radial exterior weld interface feature 220 of the examples is configured to accept a non-axially directed portion of a conductive wire disposed within an interior space of terminal 200 defined by inner surface 212. For example, a portion of a conductive wire directed according arrow 201 (e.g., directed off-axis with respect to axis A, such as approximately radially with respect to axis A) shown in FIG. 2B may be accepted in radial exterior weld interface feature 220 of terminal 200-1 for interfacing a conductor thereof with weld location 222. The illustration of FIGS. 2C and 2D show an example of a non-axially directed portion of a conductive wire accommodated in radial exterior weld interface feature 220 of terminal 200-2. In particular, non-axially directed conductive wire portion 230 of FIG. 2D is shown as having been accepted in radial exterior weld interface feature 220 of terminal 200-2 (e.g., non-axially directed conductive wire portion 230 traverses from the inner space defined by inner surface 212 to outer surface 211 via radial exterior weld interface feature 220) for interfacing conductor 231 thereof with weld location 222.

Terminals 200 including radial exterior weld interface feature 220 of embodiments are, for example, well suited for use with respect to medical device lead implementations utilizing non-axially directed conductive wires in the form of helically wound wires (e.g., conductive wires having a helix axis along a same direction as axis A of annular conductive structure 210) for connecting electrical contacts and respective neurostimulation electrodes of implantable electrical stimulation leads. Such helically wound wires, although providing a medical device lead configuration which is resilient with respect to some stretching and bending of the lead in a tight radius, may nevertheless be challenging to properly position and weld to inner surface 212 (e.g., through blind welding techniques). However, truncated aperture 221 of radial exterior weld interface feature 220 of embodiments facilitates positioning and welding a portion of non-axially directed conductive wire to outer surface 211 of terminals 200.

Weld location 222 of the examples shown in FIGS. 2A-2D is disposed on outer surface 211 of annular conductive structure 210 allow the conductor of a conductive wire (e.g., conductor 231 of non-axially directed conductive wire portion 230 shown in FIGS. 2C and 2D) to be welded to terminals 200 with a non-blind weld. For example, truncated aperture 221 of embodiments is configured for a non-axially directed portion of a conductive wire to traverse from the inner space to outer surface 211 so that a conductor of the conductive wire may be welded to weld location 222 on outer surface 211.

A laser welding process or a resistance welding process may, for example, be used to weld a conductor at weld location 222 (e.g., on outer surface 211 of annular conductive structure 210) of terminal 200-1 and terminal 200-2 without implementing a blind welding technique. Accordingly, the radial exterior weld terminal configurations of terminals 200 may accommodate welding process fixturing for directly visible welding. The ability to utilize such welding process fixturing may facilitate improved consistency and reliability with respect to the welds. For example, resistance welding apparatus may better engage the conductor of a conductive wire to consistently and reliably weld the conductor to weld location 222 on outer surface 211 of terminals 200. Moreover, welding location 222 disposed on outer surface 211 according to embodiments allows for the weld to be readily inspected.

One or more aspects of radial exterior weld interface feature 220 may be variously configured for facilitating electrically coupling a conductor of conductive wires to terminals 200 according to embodiments of the invention. For example, truncated aperture 222 may be configured to avoid damage to the conductive wires, reduce or mitigate stress on a conductor of the conductive wires, facilitate a wire traversing from an interior space to the outer surface, etc. In accordance with some embodiments of the invention, one or more edges of truncated aperture 222 may be tapered (e.g., radiused, chamfered, ramped, beveled, etc.) to accommodate the non-axially directed portion of the conductive wire traversing from the inner space to the outer surface without damage, with reduced stresses placed on a conductor, and/or minimize the space needed within an interior space of the terminal for facilitating welding of the conductor to the terminal.

Radial exterior weld interface feature 220 of the radial exterior weld terminal configuration of terminal 200-1, for example, comprises a ramped edge configuration (e.g., a ramped profile at weld location 222, as shown in FIG. 2B) configured to accommodate the non-axially directed portion of the conductive wire traversing from the inner space to the outer surface without damage while minimize the space needed within an interior space of the terminal for facilitating welding of the conductor to the terminal. The ramped edge configuration of radial exterior weld interface feature 222 of the example of terminal 200-1 further provides a weld location receiving surface substantially corresponding to the direction of a non-axially directed portion of a conductive wire to be interfaced therewith, and thus may be utilized to reduce stresses placed on the conductor.

In another example, radial exterior weld interface feature 220 of the radial exterior weld terminal configuration of terminal 200-2 comprises a recessed edge configuration (e.g., a dimpled profile at weld location 222, as shown in FIG. 2D) configured to accommodate the non-axially directed portion of the conductive wire traversing from the inner space to the outer surface. In particular, weld location 222 of terminal 200-2 is disposed on dimple member 223 depressed into the interior space of annular conductive structure 210. The dimple member provides weld location receiving surface configured to facilitate a portion of a conductive wire traversing from the interior space for a conductor thereof to interface with outer surface 211. For example, the dimple member of embodiments is recessed such that a surface of weld location 222 substantially corresponds to the direction of conductor 231 of non-axially directed conductive wire portion 230. Non-axially directed conductive wire portion 230 may thus be accommodated by radial exterior weld interface feature 220, and conductor 231 welded to weld location 222, with minimal stress on the conductor and without damage to the conductive wire. Moreover, the depression of the dimple member of embodiments protrudes minimally (e.g., on the order of 0-0.2 mm), thus minimizing or mitigating the use of space needed within an interior space of terminal 200-2 for facilitating welding of conductor 231 to the terminal.

It should be appreciated that the radial exterior weld terminal configurations of the embodiments of terminals 200 shown in FIGS. 2A-2D facilitate relatively small diameter terminal implementations (e.g., terminal outer diameters on the order of 1 mm) while providing suitable space for readily accommodating additional structures (e.g., additional conductive wires, axial lumen, stylet, etc.) within the interior space of the annular conductive structure. For example, in addition to a conductive wire associated with the terminal, the respective conductive wires for one or more additional terminals may be accommodated within annular conductive structure 210 of terminals 200. In accordance with some examples, in addition to a plurality of conductive wires being disposed within an interior space of an annular conductive structure, an axial lumen may also be provided through the interior space.

Figure 3:
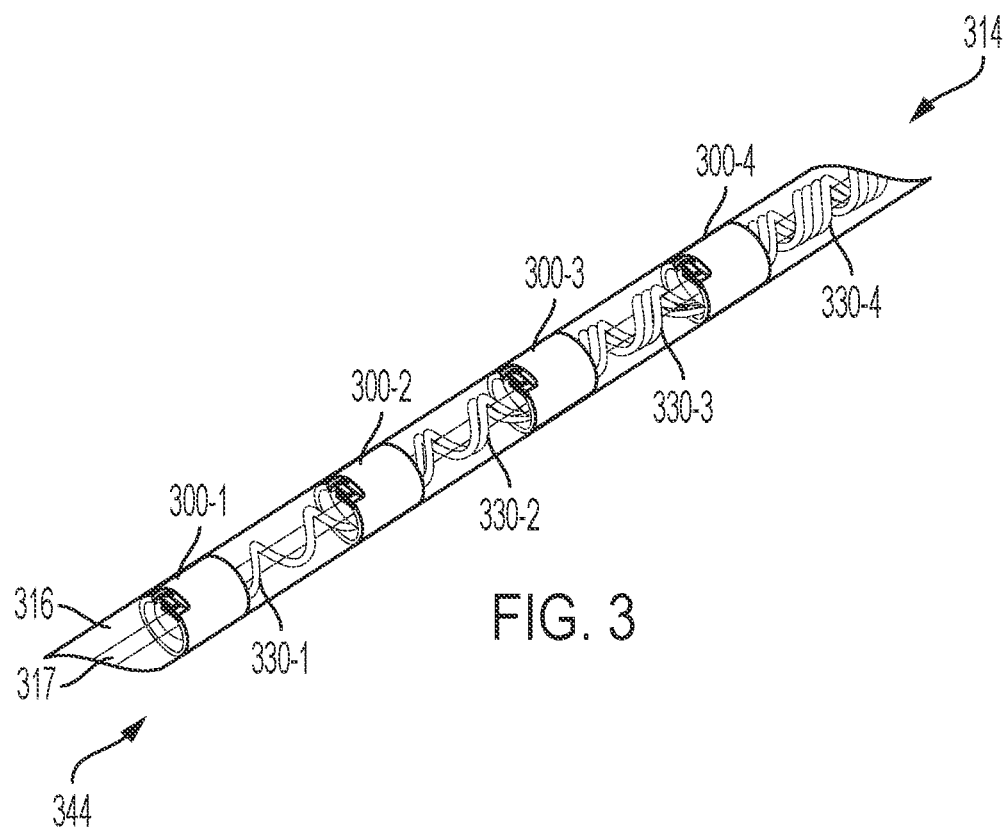
FIG. 3 shows an example medical device lead implementation including radial exterior weld terminals of embodiments of the present invention.

An example medical device lead implementation including radial exterior weld terminals according to concepts herein in a neurostimulation electrode array is shown as electrical stimulation lead 314 of FIG. 3. Electrical stimulation lead 314 may, for example, be utilized as a medical device lead (e.g., electrical stimulation lead 14) of stimulation system 10 of FIGS. 1A and 1B. Electrical stimulation lead 314 includes elongated body 316 (only distal end 344 of which is visible in FIG. 3). An array of neurostimulation electrodes (e.g., corresponding to neurostimulation electrodes 18 of stimulation system 10), comprising terminals 300-1 through 300-4, are disposed at distal end 344.

Figure 4:
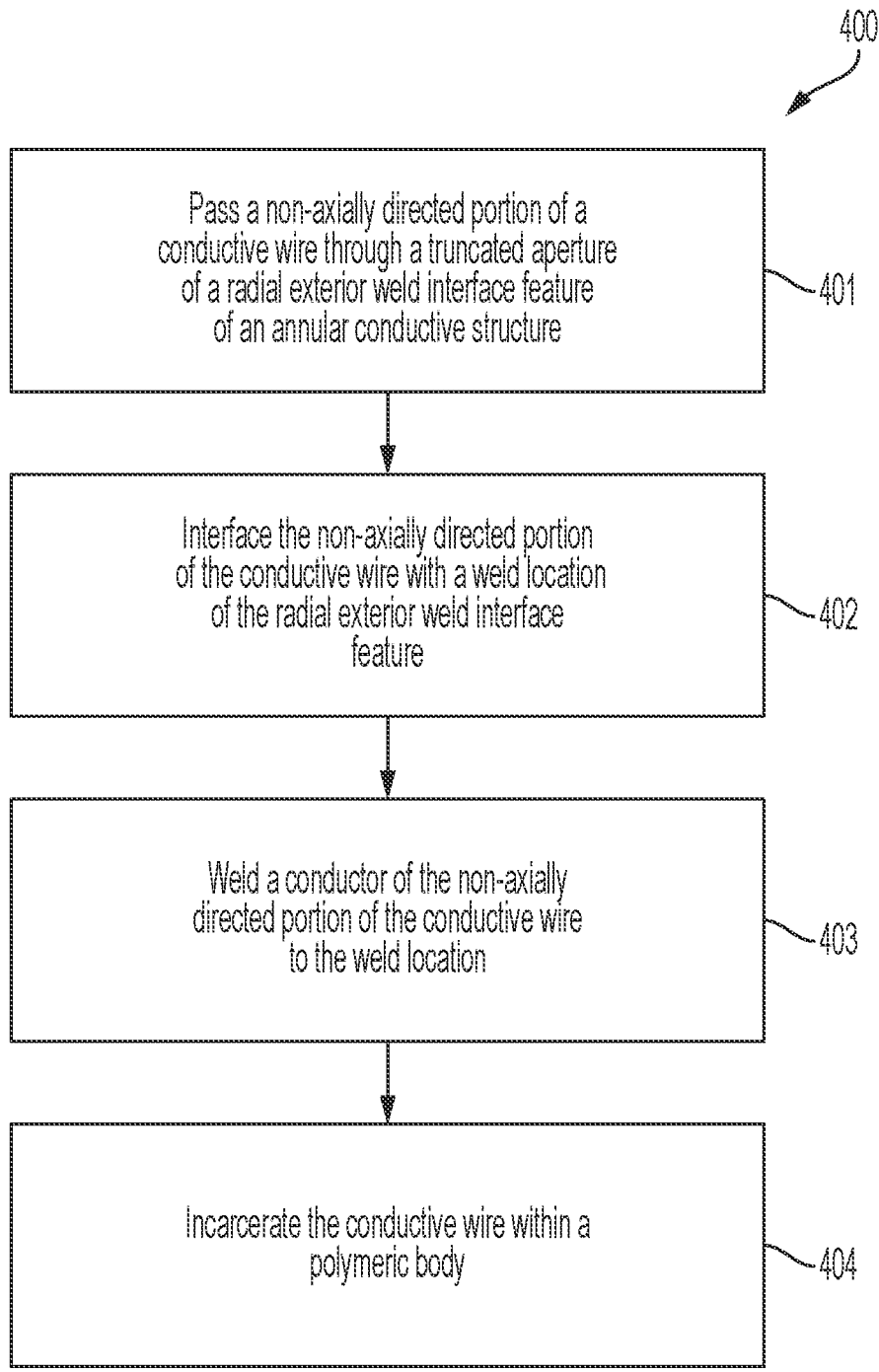
FIG. 4 shows a block diagram of a flow for forming an electrical stimulation lead including radial exterior weld terminals of embodiments of the present invention.

Electrical stimulation lead 314 may, for example, be formed in accordance with the functions of flow 400 shown in FIG. 4. At block 401 of flow 400, for each terminal of terminals 300-1 through 300-4, a non-axially directed portion of a respective conductive wire may be passed through a truncated aperture of a radial exterior weld interface feature of an annular conductive structure of the terminal. For example, a non-axially directed portion of conductive wires 330-1 through 330-4 disposed within an interior space of a respective one of terminals 300-1 through 300-4 may be passed through truncated aperture 221 of a radial exterior weld interface feature 220 disposed at a first end of annular conductive structure 210 of the terminal. In accordance with some examples, one or more of conductive wires 330-1 through 330-4 may comprise helically wound wires (e.g., a helically wound wire having a helix axis directed along a same direction as the axis of annular conductive structure 210 and elongated body 316). The non-axially directed portion of the conductive wire may comprise a helically wound portion of conductive wire.

The truncated aperture of embodiments is configured for the non-axially directed portion of the respective conductive wire to traverse from the inner space of the terminal to the outer surface for interfacing with a weld location of the radial exterior weld interface feature. In accordance with some examples, the truncated aperture and corresponding weld location of the radial exterior weld interface feature are sized, positioned, shaped, and/or oriented to assist in positioning the portion of the non-axially directed conductive wire passed through the truncated aperture for later functions (e.g., welding of the conductor). For example, embodiments of a radial exterior weld interface feature are configured to perform as a fixture to hold the conductive wire, such as for welding and/or other functions to be performed later.

In the illustrated example, terminal 300-1 is disposed more towards distal end 344 of elongated body 316 and each of terminals 300-2 through 300-4 is disposed incrementally more towards the proximal end (not shown) of elongated body 316 (e.g., more near corresponding electrical contacts, not shown, disposed on the proximal end of electrical stimulation lead 14). Accordingly, although an interior space of terminal 300-1 of the example has only its respective conductive wire (e.g., conductive wire 330-1) within its interior space, each of terminals 300-2, 300-3, and 300-4 has it respective conductive wire and one or more additional conductive wires within its interior space. In particular, terminal 300-2 of the example includes its respective conductive wire (e.g., conductive wire 330-2) and a conductive wire associated with terminal 300-1 (e.g., conductive wire 330-1). Terminal 300-3 of the example includes its respective conductive wire (e.g., conductive wire 330-3) and a conductive wire associated with each of terminals 300-1 and 300-2 (e.g., conductive wires 330-1 and 330-2). Terminal 300-4 of the example includes its respective conductive wire (e.g., conductive wire 330-4) and a conductive wire associated with each of terminals 300-1, 300-2, and 300-3 (e.g., conductive wires 330-1, 330-2, and 330-3).

At block 402 of flow 400 for each terminal of terminals 300-1 through 300-4, the non-axially directed portion of the conductive wire may be interfaced with a weld location of the radial exterior weld interface feature. For example, weld location 222 of embodiments is on outer surface 211 of annular conductive structure 210 and the non-axially directed portion of conductive wires 330-1 through 330-4 passed through truncated aperture 221 of a respective one of terminals 300-1 through 300-4 may be placed in contact with or otherwise interfaced with a corresponding weld location of radial exterior weld interface feature 220. In accordance with some examples, the non-axial directed portions of conductive wires 330-1 through 330-4 that are interfaced with weld locations 222 are disposed to accommodate welding process fixturing for directly visible welding of their conductor to annular conductive structure 210.

At block 403 of flow 400 for each terminal of terminals 300-1 through 300-4, a conductor of the non-axially directed portion of the conductive wire may be welded to the weld location. For example, conductor 231 of each of conductive wires 330-1 through 330-4 may be welded to weld location 222 of a respective one of terminals 300-1 through 330-4. In accordance with some examples, a laser welding process or a resistance welding process may be used to weld the conductor of conductive wires 330-1 through 330-4 at the weld locations of a respective one of terminals 300-1 through 300-4 without implementing a blind welding technique. Where a resistance welding process is utilized, the insulation of the conductive wire may remain in position around the conductor until ablated or otherwise displaced by the welding process. The resulting welded conductor configuration provided according to embodiments of the invention enable a tail portion of the conductor to be positioned to extend radially beyond the weld location, and thus neither the weld nor the tail portion are disposed inside of the interior space of the respective terminal.

Electrical stimulation lead 314 of embodiments may have a relatively small outside diameter, such as for use with needle guided implantation techniques. For example, electrical stimulation lead 314 of some embodiments may comprise a medical device lead configured (e.g., having an outer diameter of 1 mm to 1.4 mm) for use in PNS techniques and/or SCS techniques, lead bodies and electrodes. Accordingly, the inner diameters of terminals 300 may be relatively small (e.g., annular conductive surface ID<1 mm to 1.4 mm). The conductive wires passing within the inner spaces of the terminals may thus be in very close proximity to one another and/or other structure of the terminals. Such closely disposed conductive wires may be susceptible to having their insulation layer punctured, such as by wire strand(s) of a tail portion of a welded conductor, a rough surface of a weld bead, etc., and associated undesired interaction (e.g., electrical short circuits) between the electrode channels.

The radial exterior weld terminal configuration of terminals 300 of electrical stimulation lead 314 provide for a conductor being welded on an outer surface of the terminal. This configuration provides an implementation in which conductive wires are protected from damage due to a rough surface or other attribute of the weld bead formed with respect to a conductor welded to the terminal. Moreover, the weld of the conductor to the terminal is also protected for damage or other interference by one or more other conductive wires within the interior space of the terminal. Further, the full extent of a tail portion of the conductor that extends radially beyond the weld is disposed outside of the inner space of the terminal, further protecting conductive wires therein from damage.

Elongated body 316 may be composed of an electrically insulative material (e.g., polyurethane or silicone) incarcerating conductive wires 330-1 through 330-4 and/or providing a unitary body structure retaining terminals 300-1 through 300-4 (and, according to some embodiments, corresponding electrical contacts at a proximal end of electrical stimulation lead 314) in their relative positions. For example, terminals 300 may be placed over a mandrel and the functions of blocks 401-403 described above performed to implement desired electrical connectivity of the various electrode channels. Thereafter, at block 404 of flow 400, conductive wires may be incarcerated within a polymeric body. For example, each of conductive wires 330-1 through 330-4 may be incarcerated within polymer of elongated body 316 extending from both ends of annular conductive structure 201 of the respective terminals 300-1 through 300-4. In accordance with some examples, a polymer of elongated body 316 may be molded over a mandrel over which terminals 300 are placed to thereby encapsulate conductive wires 330-1 through 330-4 within the polymer material. A diameter of elongated body 316 may substantially correspond to the outer diameter of terminals 300 (e.g., having an outer diameter of 1 mm to 1.4 mm in the above PNS and/or SCS examples). Axial lumen 317 may be provided within elongated body 316 upon removal of elongated body 316 from the mandrel of such an embodiment.

Figure 5:
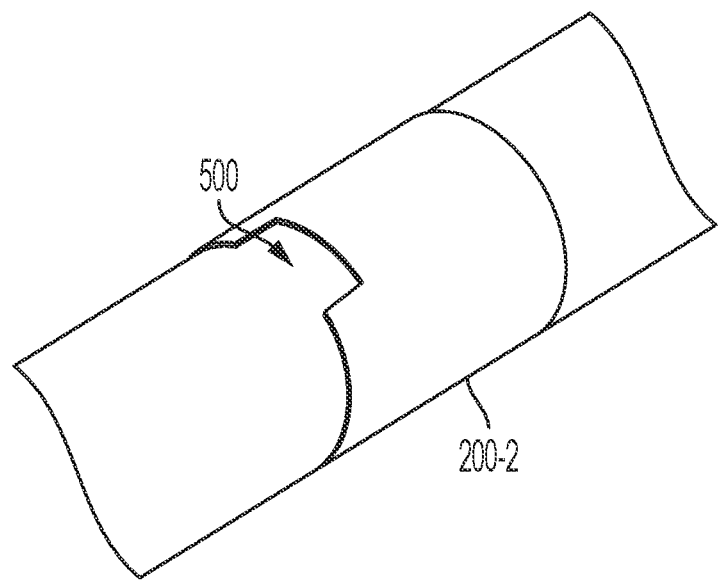
FIG. 5 shows a weld area of an example of a radial exterior weld terminal covered with polymer after welding according to embodiments of the present invention.

In accordance with embodiments of the invention, the conductor of a non-axially directed portion of conductive wire that is welded to the outer surface of the annular conductive structure at the weld location is covered with a polymer forming the polymeric body. For example, as shown in FIG. 5, a weld area of the example of terminal 200-2 of FIGS. 2C and 2D may be covered with polymer of the elongated body after welding and inspection. In accordance with this recessed edge configuration (e.g., a dimpled profile at weld location 222), the polymer material of the elongated body may nevertheless substantially conform to the uniformity of the circumferences between the elongated body and the annular conductive structure of the terminal. It should be appreciated, however, that a tapered configuration of the example of terminal 200-1 of FIGS. 2A and 2B may likewise provide an implementation in which the weld area may be covered with polymer of the elongated body after welding and inspection. Although, there may be a detectable lack of complete uniformity of the circumferences between the elongated body and the annular conductive structure of the terminal at the weld location of some implementations of the radial exterior weld terminal configuration of terminal 200-1.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. A medical device lead comprising:
a conductive wire having a non-axially directed portion and a conductor;
a terminal including an annular conductive structure having an outer surface and an inner surface radially disposed with respect to an axis of the annular conductive structure, the annular conductive structure having a radial exterior weld interface feature disposed at a first end of the annular conductive structure and comprising:
a weld location on the outer surface at the first end of the annular conductive structure and comprising a first tapered portion of the annular conductive structure terminating at a first side of the weld location, wherein the first tapered portion is tapered in a direction substantially corresponding to the direction of the non-axially directed portion of the conductive wire; and
a truncated aperture formed in the first end of the annular conductive structure having an aperture opening at the first end of the annular conductive structure and providing a second tapered portion of the annular conductive structure at a first side of the truncated aperture in juxtaposition with the first side of the weld location,
wherein the second tapered portion is tapered in the direction substantially corresponding to the direction of the non-axially directed portion of the conductive wire, and
wherein the truncated aperture is configured for passing the non-axially directed portion of the conductive wire from within an interior space of the terminal defined by the inner surface at a position between the first side of the truncated aperture and the first side of the weld location to interface the conductor of the non-axially directed portion of the conductive wire with the weld location on the outer surface, and
wherein the non-axially directed portion of the conductive wire is directed off-axis with respect to the axis of the annular conductive structure; and
a polymeric body extending from both the first end of the annular conductive structure and a second end of the annular conductive structure.

2. The medical device lead of claim 1, wherein the first tapered portion and the second tapered portion are tapered to accommodate the non-axially directed portion of the conductive wire traversing from the interior space to the outer surface without damage to the conductive wire.

3. The medical device lead of claim 1,
wherein the conductor of the non-axially directed portion of the conductive wire is welded to the outer surface of the annular conductive structure at the weld location and is covered with a polymer forming the polymeric body.

4. The medical device lead of claim 3, wherein the polymer forming the polymeric body substantially conforms to a circumference of the polymeric body to a circumference of the annular conductive structure of the terminal.

5. The medical device lead of claim 3, wherein the radial exterior weld interface feature comprising the weld location on the outer surface and the truncated aperture formed in the first end of the annular conductive structure is configured for the annular conductive structure accommodating additional conductive wires and an axial lumen within the interior space of the terminal.

6. The medical device lead of claim 1, wherein the conductor of the non-axially directed portion of the conductive wire is welded to the outer surface of the annular conductive structure at the weld location and a tail portion of the conductor extending radially beyond the weld location is disposed outside of the interior space of the terminal.

7. The medical device lead of claim 1, wherein the non-axially directed portion of the conductive wire comprises a portion of a helically wound wire, and wherein a helix axis of the helically wound wire is along a same direction as the axis of the annular conductive structure.

8. The medical device lead of claim 1, wherein the terminal comprises a neurostimulation electrode.

9. The medical device lead of claim 1, wherein the terminal comprises an electrical contact configured to electrically couple the medical device lead to an implantable pulse generator.

10. The medical device lead of claim 1, wherein the first tapered portion is configured to minimize the space needed within the interior space of the terminal for facilitating welding of the conductor to the terminal.

11. The medical device lead of claim 1, wherein the first tapered portion comprises a ramped edge configuration.

12. The medical device lead of claim 11, wherein the ramped edge configuration comprises a weld location receiving surface for reducing stresses placed on the conductor of the non-axially directed portion of the conductive wire.

13. The medical device lead of claim 11, wherein the ramped edge configuration does not protrude into the interior space of the terminal.

14. The medical device lead of claim 1, wherein the first tapered portion comprises a recessed edge configuration.

15. The medical device lead of claim 1, wherein the first tapered portion and the second tapered portion shape the truncated aperture and the weld location to assist in positioning the non-axially directed portion of the conductive wire for welding the conductor to the weld location on the outer surface of the annular conductive structure.

16. A neurostimulation system comprising:
an implantable pulse generator; and
an implantable medical electrical stimulation lead comprising:
a plurality of conductive wires, each conductive wire of the plurality of conductive wires having a non-axially directed portion and a conductor;
a plurality of neurostimulation electrodes in electrical communication with the implantable pulse generator via respective conductive wires of the plurality of conductive wires, wherein each neurostimulation electrode of the plurality of neurostimulation electrodes includes:
an annular conductive structure having an outer surface and an inner surface radially disposed with respect to an axis of the annular conductive structure, the annular conductive structure having a radial exterior weld interface feature disposed at a first end of the annular conductive structure and comprising:

a weld location on the outer surface at the first end of the annular conductive structure and comprising a first tapered portion of the annular conductive structure terminating at a first side of the weld location, wherein the first tapered portion is tapered in a direction substantially corresponding to the direction of the non-axially directed portion of the conductive wire; and a truncated aperture formed in the first end of the annular conductive structure having an aperture opening at the first end of the annular conductive structure and providing a second tapered portion of the annular conductive structure at a first side of the truncated aperture in juxtaposition with the first side of the weld location, wherein the second tapered portion is tapered in the direction substantially corresponding to the direction of the non-axially directed portion of the conductive wire, wherein the truncated aperture is configured for passing the non-axially directed portion of the respective conductive wire of the respective conductive wires from within an interior space of the neurostimulation electrode defined by the inner surface at a position between the first side of the truncated aperture and the first side of the weld location to interface the conductor of the non-axially directed portion of the respective conductive wire with the weld location on the outer surface, and wherein the non-axially directed portion of the respective conductive wire is directed off-axis with respect to the axis of the annular conductive structure; and a polymeric body extending from both the first end of the annular conductive structure and a second end of the annular conductive structure.

17. The neurostimulation system of claim 16, wherein the conductor of the non-axially directed portion of the respective conductive wire is welded to the outer surface of the annular conductive structure at the weld location and a tail portion of the conductor extending radially beyond the weld location is disposed outside of the interior space of the neurostimulation electrode.

18. The neurostimulation system of claim 16, wherein each respective conductive wire of the respective conductive wires comprises a helically wound wire, and wherein a helix axis of the helically wound wire is along a same direction as the axis of the annular conductive structure.

19. The neurostimulation system of claim 16, wherein the first tapered portion comprises a ramped edge configuration.

\* \* \* \* \*